(12) United States Patent
Thibaut et al.

(10) Patent No.: US 6,740,694 B2
(45) Date of Patent: May 25, 2004

(54) PREPARATION OF LOW-DUST STABILISERS

(75) Inventors: Daniel Thibaut, Michelbach-le-Bas (FR); André Schmitter, Hegenheim (FR); Benjamin Breitenstein, Rheinfelden (CH); Christoph Kleiner, Wölflinswil (CH); Matthias von Frieling, Weil am Rhein (DE); Martin von Büren, Muttenz (CH); André Geoffroy, Habsheim (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 131 days.

(21) Appl. No.: 09/815,620

(22) Filed: Mar. 23, 2001

(65) Prior Publication Data

US 2001/0023269 A1 Sep. 20, 2001

Related U.S. Application Data

(62) Division of application No. 09/059,148, filed on Apr. 13, 1998, now Pat. No. 6,225,375.

(30) Foreign Application Priority Data

Apr. 15, 1997 (CH) .............................. 874/97
May 6, 1997 (CH) .............................. 1055/97
Jan. 20, 1998 (CH) .............................. 125/98

(51) Int. Cl.$^7$ .......................... C08K 5/34; C08K 15/32
(52) U.S. Cl. ............. 524/94; 252/400.23; 252/400.24; 252/401; 252/407; 523/223; 524/94; 524/100; 524/102; 548/257
(58) Field of Search ........................ 252/400.23, 400.24, 252/401, 407; 523/223; 524/99, 100, 102; 548/257

(56) References Cited

U.S. PATENT DOCUMENTS

| | | | |
|---|---|---|---|
| 4,001,266 A | 1/1977 | Rody et al. ................. 260/308 |
| 4,041,044 A | 8/1977 | White ........................ 260/308 |
| 4,219,480 A | 8/1980 | White et al. ................ 548/260 |
| 4,230,867 A | 10/1980 | Kintopf et al. ............. 548/260 |
| 4,683,326 A | 7/1987 | Orban et al. ................ 560/75 |
| 4,739,102 A | 4/1988 | Tokunaga .................... 560/75 |
| 4,999,433 A | 3/1991 | Prestel et al. .............. 548/260 |
| 5,238,605 A | 8/1993 | Abeler et al. ............ 252/400.1 |
| 5,276,076 A | 1/1994 | Pastor et al. ............... 524/119 |
| 5,373,040 A | 12/1994 | Pastor et al. ............... 524/119 |
| 5,468,895 A | * 11/1995 | Mahood ...................... 524/117 |
| 5,489,636 A | 2/1996 | Shum et al. ................. 524/119 |
| 5,574,166 A | 11/1996 | Winter et al. ............... 548/260 |
| 5,597,857 A | 1/1997 | Thibaut et al. .............. 524/400 |

FOREIGN PATENT DOCUMENTS

| | | |
|---|---|---|
| DE | 19541242 | 5/1997 |
| EP | 0255743 | 2/1988 |
| EP | 0278579 | 8/1988 |
| EP | 0281189 | 9/1988 |
| EP | 0514784 | 11/1992 |
| EP | 0565184 | 10/1993 |
| EP | 0392392 | 12/1995 |
| EP | 771360 | 5/1997 |
| GB | 2267499 | 12/1993 |
| JP | 59-104348 | 6/1984 |

OTHER PUBLICATIONS

Derwent Abstract 95–332512/43 for JP 07228577, Feb. 16, 1994.
Derwent Abstract 95–332511/43 for JP 07228576, Feb. 16, 1994.
Derwent Abstract 95–136827/18 for JP 07061976, Aug. 26, 1993.
Derwent Abstract 92–231926/28 for JP 04159268, Jun. 2, 1992.
Derwent Abstract 89–126044/17 for JP 01071862, Sep. 11, 1987.
Derwent Abstact 86–315455/48 for JP 61233677, Apr. 9, 1985.
Derwent Abstract 88–254873/36 for JP 63186886, Jan. 27, 1987.
Derwent Abstract 77009 D/42 for JP 56113772, Feb. 13, 1980.
Derwent Abstract 86–295750/45 for JP 61218577, Mar. 22, 1985.
Derwent Abstract 78705Y/44 for JP 52113973, Mar. 19, 1976.
Derwent Abstract 50733A/28 for JP 53063379, Nov. 17, 1976.
Derwent Abstract 01127 J/47 for JP 57167976, Apr. 9, 1981.
Derwent Abstract 85–277809/45 for EP 160246, Apr. 16, 1984.
Derwent Abstract 86–229955/35 for JP 61161269, Jan. 10, 1985.
Derwent Abstract 86–269552/41 for JP 61197570, Feb. 27, 1985.
Derwent Abstract 86–294506/45 for JP 61215379, Mar. 19, 1985.
Derwent Abstract 90–287146/38 for JP 02202877, Jan. 31, 1989.

(List continued on next page.)

Primary Examiner—Kriellion A. Sanders
(74) Attorney, Agent, or Firm—Tyler A. Stevenson; Kevin T. Mansfield

(57) ABSTRACT

A description is given of an extrusion process for the preparation of a low-dust stabiliser, using a subcooled melt as granulation liquid, as well as of novel amorphous modifications of different stabilisers, including 2,2'-methylenebis (4-[1,1,3,3-tetramethylbutyl]-6-benzotriazol-2-yl-phenol), and of the β-crystalline modification of 2-(2-hydroxy-3,5-di-tert-butylphenyl)-5-chlorobenzotriazole and of the preparation thereof. The novel process affords products which are easy to handle and which are flowable, and the novel modifications have advantages as regards their preparation, processing and their use as stabiliser.

18 Claims, No Drawings

OTHER PUBLICATIONS

Derwent Abstrract 90-287147/38 for JP 02202878, Jan. 31, 1989.
Derwent Abstract 90-37480/51 for JP 02273677, Apr. 14, 1989.
Derwent Abstract 95-380049/49 for JP 07258229, Mar. 25, 1994.
Derwent Abstract 96-439548/44 for JP 08217762, Feb. 16, 1995.
Derwent Abstract 88-324473/46 for DE 3731860, Apr. 22, 1987.
Derwent Abstract 90-109608/15 for EP 363318, Sep. 28, 1988.

* cited by examiner

PREPARATION OF LOW-DUST STABILISERS

This is a divisional of application Ser. No. 09/059,148, filed on Apr. 13, 1998, now U.S. Pat. No. 6,225,375.

The present invention relates to a process for the preparation of low-dust stabilisers by extruding a subcooled melt, to the use of the products of this process for stabilising organic polymers, to novel amorphous modifications, e.g. of 2,2'-methylenebis(4-[1,1,3,3-tetramethylbutyl]-6-benzotriazol-2-yl-phenol), to a novel crystalline modification of 2-(2-hydroxy-3,5-di-tert-butylphenyl)-5-chlorobenzotriazole, to a process for its preparation and processing as well as to compositions stabilised therewith.

The development of stabiliser which are low-dust and therefore generally easier to handle has been pursued for some time; specific stabilisers have, inter alia, been mounted on inorganic substrates (e.g. U.S. Pat. No. 5,238,605).

GB-A-2267499 describes the preparation of a mixture of tetraalkylpiperidine type stabilisers of high and low molecular weight by mixing in a melted state.

U.S. Pat. No. 5,597,857 describes a process for the preparation of low-dust stabilisers by extruding a calcium stearate melt; JP-A-59-104348 and EP-A-565184 also propose extruding a melt. DE-A-19541242 proposes pastillising a mixture consisting of crystalline and melted plastic additives.

The use of a regular melt during extrusion is only possible to a limited degree owing to its low viscosity.

Amorphous modifications of individual stabilisers and their use for stabilising organic polymers have already been described, inter alia, in EP-A-278579, U.S. Pat. No. 4,683,326, EP-A-255743, U.S. Pat. No. 5,373,040, U.S. Pat. No. 5,489,636, JP-A-59-104348, U.S. Pat. No. 5,574,166. They are usually prepared by rapidly cooling (chilling) the melt to prevent crystallisation. EP-A-278579 describes the preparation of a partially crystalline stabiliser mixture consisting of amorphous tetrakis[3-(3,5-di-tert-butyl-4-hydroxyphenyl)propionyloxymethyl]methane and a crystalline organic phosphite by subcooling the melt.

EP-A-514784 describes the extrusion of tetrakis[3-(3,5-di-tert-butyl-4-hydroxyphenyl)propionyloxymethyl]methane and the mixtures thereof with inorganic salts of fatty acid salts at temperatures in the melting range.

Surprisingly, it has now been found that the metastable state which is passed during the preparation of low molecular weight amorphous stabilisers, the subcooled melt, is excellently suitable for use as granulation liquid or binder during the extrusion. It is remarkable that the formation of crystalline modifications of the low molecular weight stabilisers is unexpectedly highly inhibited, making it possible to process the plastic extrusion compositions to granules by conventional methods.

Accordingly, this invention relates to a process for the preparation of a low-dust stabiliser, which comprises extruding a subcooled melt of a stabiliser having a molecular weight of 200 to 1500 g/mol, or the plastic composition of the mixture consisting of the subcooled melt of the stabiliser and of a crystalline stabiliser and/or other customary additives. The plastic composition therefore consists of the subcooled melt as homogeneous continuous phase and, where appropriate, of further components dispersed therein (disperse phase(s)).

The processing to marketable, low-dust, flowable and storage-stable forms with good meterability, e.g. for pelletisation, pastillation, melt granulation and compounding, is thus made substantially easier or possible at all. The moulding of the product can, for example, also be carried out before or during the cooling process by dividing the subcooled melt or the mixture, for example by dripping in the liquid state or by dividing in the plastic state with subsequent cooling. The process of this invention therefore also encompasses a process for granulating a stabiliser, which comprises extruding and dividing a subcooled melt of the stabiliser or the plastic compound consisting of the mixture of the subcooled melt of the stabiliser and of crystalline stabiliser and/or other customary additives. Solidification after extrusion gives a low-dust stabiliser, e.g. as granules.

This invention also relates to the granules obtainable by the novel process as well as to the use of a subcooled melt for extruding a stabiliser or stabiliser mixture, in particular for pelletisation, melt granulation or compounding.

The subcooled melt is single-phase and accordingly has only one single glass transition temperature; it can, however, consist of one or several chemical compounds and it preferably consists of 1 to 3 main components. Main components are to be understood as being those compounds, the proportion of which in the subcooled melt is 10% by weight or more, preferably 30% by weight or more. Also important is a subcooled melt which consists mainly, i.e. usually to 60% by weight or more, preferably to 70% by weight or more, of 1 chemical compound (weight always being based on the total weight of the homogeneous subcooled melt).

The amount of tetrakis[3-(3,5-di-tert-butyl-4-hydroxyphenyl)propionyloxymethyl]methane in the subcooled melt is preferably less than 80% by weight, more preferably from 0–60% by weight. A particularly important process of this invention is that, wherein tetrakis[3-(3,5-di-tert-butyl-4-hydroxyphenyl)propionyloxymethyl]methane is not a main component of the subcooled melt.

The molecular weight of the chemical compounds forming the subcooled melt (main components) is usually 300–1200 g/mol, preferably 300–1000 g/mol, particularly preferably 500–1000 g/mol. These chemical compounds are normally one or several organic compounds, for example hydrocarbons containing 6 to 100 carbon atoms and, where appropriate, 1 to 30 hetero atoms, such as O, N, S, P, halogen. The melting point (m.p.) of the chemical compound, which forms a main component, preferably any component present to more than 5% by weight, is usually 130° C. or higher, preferably 140° C. or higher, more preferably 170° C. or higher, and the glass transition temperature ($T_G$) is in the range from 10–120° C., preferably from 20–100° C. The ratio of glass transition temperature ($T_G$) to melting point (m.p.), each measured in Kelvin (K), is preferably in the range from 0.6 to 0.9; more preferably in the range from 0.65 to 0.85.

The compounds which form the subcooled melt are usually light stabilisers or antioxidants, for example those cited in the list given hereinbelow under the items 1, 2 and 4, provided they meet the stated criteria regarding molecular weight, melting point and glass transition temperature. They preferably belong to the class consisting of UV absorbers, sterically hindered amines (HALS), phenolic antioxidants, phosphites, phosphonites, lactones. In the novel process it is generally possible to use those compounds which, by themselves or as mixtures, are obtainable also in single-phase amorphous form by chilling the melt.

The following compounds are preferably used in the novel process:

1) 2,2'-methylenebis(4-[1,1,3,3-tetramethylbutyl]-6-benzotriazol-2-yl-phenol) (CAS reg. No. 103597-45-1) of formula

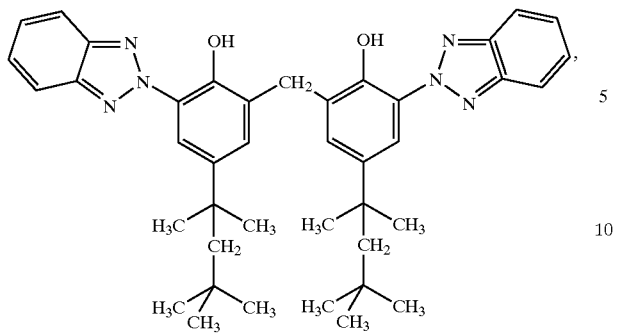

2) bis(2-methyl-4-hydroxy-5-tert-butylphenyl)sulfide (CAS reg. No. 000096-69-5),

3)

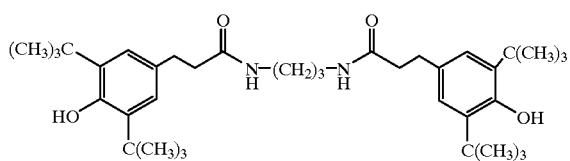

(CAS reg. No. 069851-61-2),

4) N,N'-bis(3-[3',5'-di-tert-butyl-4'-hydroxyphenyl] propionyl)hexamethylenediamine (CAS reg. No. 023128-74-7), 5) 1,3,5-trimethyl-2,4,6-tris(3',5'-di-tert-butyl-4'-hydroxybenzyl)benzene (CAS reg. No. 001709-70-2), 6) 1,3,5-tris(3,5-di-tert-butyl-4-hydroxybenzyl)-1,3,5-triazine-2,4,6(1H,3H,5H)trione (CAS reg. No. 027676-62-6),

7)

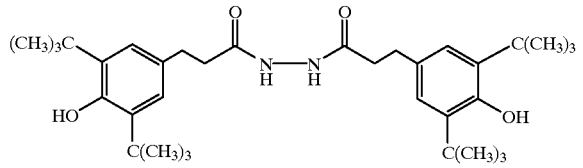

(CAS reg. No. 032687-78-8), 8) 1,3,5-tris(4-tert-butyl-3-hydroxy-2,6-dimethylbenzyl) 1,3,5-triazine-2,4,6-(1H,3H,5H)trione (CAS reg. No. 040601-76-1), 9) di(1,2,2,6,6-pentamethylpiperidin-4-yl)-2-(3,5-di-tert-butyl-4-hydroxybenzyl)-2-n-butylmalonate (CAS reg. No. 063843-89-0), 10) 2-(2'-hydroxy-3',5'-bis(1,1-dimethylbenzyl)phenyl) benzotriazole (CAS reg. No. 070321-86-7) of formula

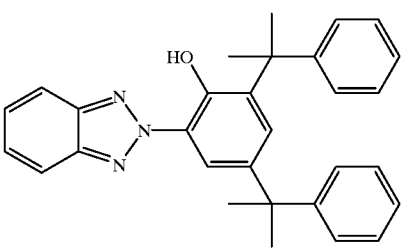

11) 2-(2'-hydroxy-3',5'-di-tert-butylphenyl)benzotriazole (CAS reg. No.003846-71-7);

12) isomeric mixtures (CAS reg. No. 181314-48-7) consisting of about 85% by weight of 5,7-di-tert-butyl-3-(3,4-dimethylphenyl)-(9d)-2(3H)-benzofuranone and about 15% by weight of 5,7-di-tert-butyl-3-(2,3-dimethylphenyl)-(9d)-2(3H)-benzofuranone;

13) pentaerythritol-tetrakis(3-[3',5'-di-tert-butyl-4'-hydroxyphenyl]propionate) (CAS reg. No. 006683-19-8);

14) 2-(2-hydroxy-3,5-di-tert-butylphenyl)-5-chlorobenzotriazole (CAS reg. No. 3864-99-1)

15)

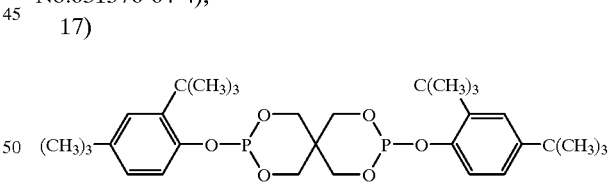

(CAS reg. No. 080410-33-9);

16) tris(2,4-di-tert-butylphenyl)phosphite (CAS reg. No.031570-04-4);

17)

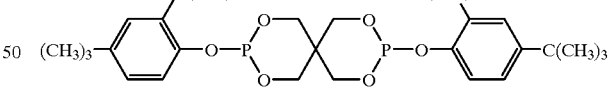

(CAS reg. No. 26741-53-7);

18)

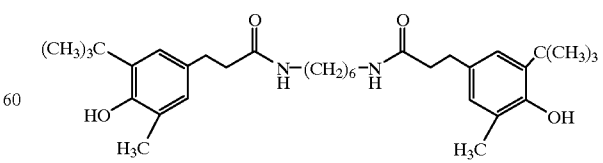

CAS reg. No. 37042-77-6);

19) 2-[2'-hydroxy-3'-(α-α-dimethylbenzyl)-5'-(1,1,3,3-tetramethyl-butyl)phenyl]benzotriazole of formula

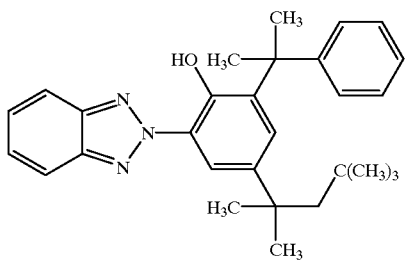

(CAS reg. No. 073936-91-1).

The following Table provides the molecular weight (Mw), melting point (m.p.; DSC +4° C./min), melt enthalpy (ΔH), glass transition temperature (Tg; DSC +20° C./min) and preferred processing temperature (Tp) of these compounds:

| compound | Mw (g/mol) | m.p. (° C.) | ΔH (J/g) | Tg (° C.) | Tp (° C.) about |
|---|---|---|---|---|---|
| 1) | 658 | 197 | 86 | 70–80 | 90–140 |
| 2) | 358 | 161 | 113 | 25–35 | 40–60 |
| 3) | 594.8 | 177 | 93 | 55–65 | 70–100 |
| 4) | 636.9 | 160 | 96.5 | 50–60 | 70–130 |
| 5) | 775 | 179/243* | 200/65* | 90–100 | 105–125 |
| 6) | 784 | 220 | 75 | 105–115 | 115–140 |
| 7) | 553 | 200/229* | 50/120* | 65–75 | 75–100 |
| 8) | 699 | 158 | 20.5 | 110–120 | 120–155 |
| 9) | 685 | 148 | 80 | 40–50 | 55–145 |
| 10) | 447.6 | 139 | 84 | 35–45 | 55–100 |
| 11) | 323.4 | 154 | 88.5 | 15–25 | 25–40 |
| 12) | 350.5 | 132 | 90 | 20–30 | 40–80 |
| 13) | 1177.6 | 105–125* | 50–72* | 40–55 | 65–95 |
| 14) | 357.9 | 157 | 80 | 20–30 | 30–40 |
| 15) | 1465 | 203 | 46.5 | 105–115 | 130–200 |
| 16) | 646.9 | 186 | 71 | 35–45 | 50–70 |
| 17) | 604 | 172 | 65 | 45–55 | 65–80 |
| 18) | 552 | 163 | ca.120 | 50–60 | 70–150 |
| 19) | 441.4 | 113 | 64–65 | 30–40 | 50–100 |

*different crystal modifications

The subcooled melt is conveniently obtained by rapidly cooling a regular melt, the final temperature being below the melting point (m.p.) of the main component, preferably below the regular melting point (m.p.) of the component having the lowest melting point (usually called only melting point hereinafter). The final temperature is preferably in the range of the processing temperature stated further on. The cooling process can be carried out in a manner known per se, for example by introducing a melt to the cooled extruder, melting the stabiliser in the extruder and then transporting the melt into a corresponding cooled zone, or by preparing the subcooled melt outside of the extruder. The melt can result direct from the synthesis of a compound or from melting one or several compounds. The subcooled melt can also be obtained by rapidly melting a solid amorphous compound to a temperature from the glass transition temperature to the melting point of the crystalline modification, preferably in the range of the processing temperature. Depending on the cooling method or cooling speed, the melt can also be processed to an amorphous or partially amorphous product, for example pellets, using a melt screw or extruder.

It has furthermore been found that the subcooled single-phase melt can surprisingly also contain a smaller proportion of compounds, for example up to 40% by weight, in particular up to 30 or 20% by weight, in dissolved form, the glass transition temperature ($T_G$) of which is below 10° C., meaning that they cannot be obtained in amorphous form by chilling processes using customary cooling temperatures up to about 0° C.; the precondition being that the glass transition temperature of the resulting phase is above 10° C., in particular above 20° C. These compounds usually also belong to the group of the light stabilisers or antioxidants as indicated above for the compounds forming the subcooled melt.

The subcooled melt and components which may be dispersed therein form the extrudable plastic composition. The subcooled melt component in the novel extrusion is preferably from 5 to 100% by weight, more preferably from 20 to 100% by weight, most preferably from 50 to 100% by weight, of the plastic composition. Other dispersed components, if present, are preferably crystalline at the processing temperature. Dispersed further components are usually conventional additives, for example the classes and products cited hereinbelow as possible co-additives. It is preferred to use, in particular, phenolic antioxidants, organic phosphites or phosphonites as well as sterically hindered amines.

Extrusion will be understood in this connection as being any process warranting a transport of the plastic composition, often via a screw, with suitable tempering. The plastic composition is usually additionally mixed and/or moulded after passage through a tempered zone, for example to granules, pellets or strands.

The plastic additives (stabilisers) are advantageously processed in a single- or twin-screw extruder. Such extruders are known in the plastics processing industry and are marketed, for example, by Buss (CH), Brabender (DE), Werner and Pfleiderer (DE) or Bühler (CH).

After or also while the still-soft extruded product is cut and after passage through a die or perforated plate, the granule particles are often cooled. Cooling can be carried out in the form of wet cooling with water (for example in water, via a water film, water ring etc.) or, preferably, with air (for example air film, air vortex etc.), or also combined. Cooling with water requires subsequent dehydration and drying (preferably in a vortex drier or fluidised-bed drier). The technical implementations of these cooling methods are known. Granulation is preferably carried out while the material is still in the plastic state, prior to the actual cooling step, in contrast to the extrusion granulation and grinding process usual in the state of the art.

The processing temperature of the plastic composition is preferably about in the middle between the regular melting point (m.p.) and the glass transition temperature ($T_G$) of the homogeneous phase. The processing temperature is preferably in the range from $T_{MIN}$ to $T_{MAX}$, where with (m.p.)−($T_G$)=Δ:

$$T_{MIN}=T_G+0.2\Delta$$

$$T_{MAX}=T_G+0.6\Delta;$$

particularly preferably:

$$T_{MIN}=T_G+0.3\Delta$$

$$T_{MAX}=T_G+0.5\Delta.$$

In other of its aspects, this invention relates to granules which are obtainable by the novel process as well as to the use of a subcooled melt of a stabiliser for extrusion, in particular for pelletisation, melt granulation or compounding.

Depending on the implementation and cooling conditions, the novel process affords a crystalline, partially crystalline or completely amorphous product.

Accordingly, this invention also relates to a single-phase amorphous stabiliser comprising 2 or more compounds having have a molecular weight in the range from 300–1000 g/mol.

Novel Amorphous Modifications

This invention also relates to novel amorphous forms of stabiliser, known so far only in their crystalline modification, namely the compounds 1) 2,2'-methylenebis(4-[1,1,3,3-tetramethylbutyl]-6-benzotriazol-2-yl-phenol) (CAS reg. No. 103597-45-1) of formula

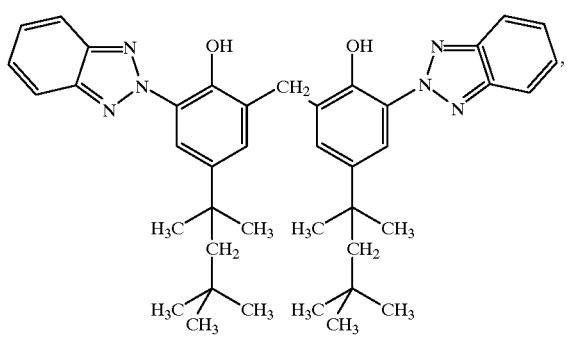

2) bis(2-methyl-4-hydroxy-5-tert-butylphenyl)sulfide (CAS reg. No. 000096-69-5),

3)

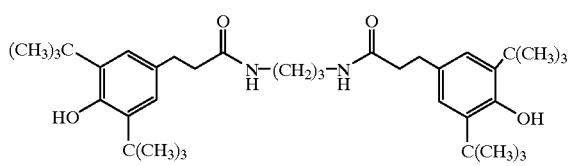

(CAS reg. No. 069851-61-2),

4) N,N'-bis(3-[3',5'-di-tert-butyl-4'-hydroxyphenyl]propionyl)hexamethylenediamine (CAS reg. No. 023128-74-7), 5) 1,3,5-trimethyl-2,4,6-tris(3',5'-di-tert-butyl-4'-hydroxybenzyl)benzene (CAS reg. No. 001709-70-2)

6) 1,3,5-tris(3,5-di-tert-butyl-4-hydroxybenzyl)-1,3,5-triazine-2,4,6(1H,3H,5H)trione (CAS reg. No. 027676-62-6)

7)

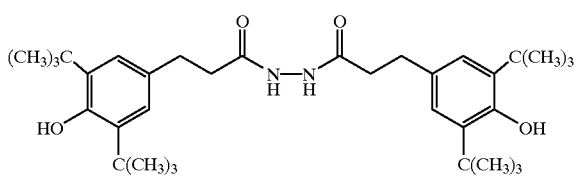

(CAS reg. No. 032687-78-8)

8) 1,3,5-tris(4-tert-butyl-3-hydroxy-2,6-dimethylbenzyl)1,3,5-triazine-2,4,6-(1H,3H,5H)trione (CAS reg. No. 040601-76-1)

9) di(1,2,2,6,6-pentamethylpiperidin-4-yl)-2-(3,5-di-tert-butyl-4-hydroxybenzyl)-2-n-butylmalonate (CAS reg. No. 063843-89-0), 10) 2-(2'-hydroxy-3',5'-bis(1,1-dimethylbenzyl)phenyl) benzotriazole (CAS reg. No. 070321-86-7) of formula

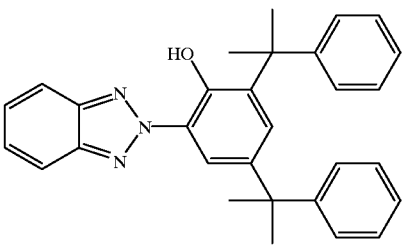

11) 2-(2'-hydroxy-3',5'-di-tert-butylphenyl)benzotriazole (CAS reg. No.003846-71-7);

12) isomeric mixture of 5,7-di-tert-butyl-3-(3,4-dimethylphenyl)-(9d)-2(3H)benzofuranone and 5,7-di-tert-butyl-3-(2,3-dimethylphenyl)-(9d)-2(3H)-benzofuranone;

14) 2-(2-hydroxy-3,5-di-tert-butylphenyl)-5-chlorobenzotriazole, synonymous with 2,4-di-tert-butyl-6-(5-chlorobenzotriazol-2-yl, phenol (CAS reg. No. 3864-99-1), of formula

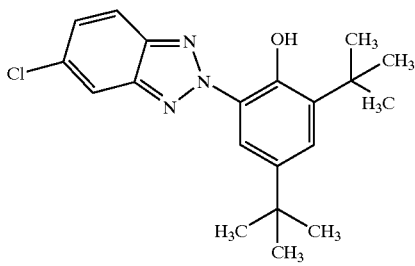

18)

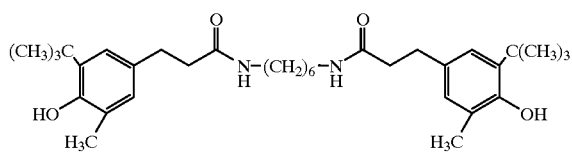

(CA-reg. No. 37042-77-6)

Compound 12, an isomeric mixture, has the CAS reg. No.181314-48-7 and consists of about 85% by weight 5,7-di-tert-butyl-3-(3,4-dimethylphenyl)-(9d)-2(3H)-benzofuranone and about 15% by weight 5,7-di-tert-butyl-3-(2,3-dimethylphenyl)-(9d)-2(3H)-benzofuranone.

These compounds are at the same time particularly preferred compounds for use in the extrusion process described at the outset.

The cited compounds are effective for stabilising organic material against the harmful action of light, heat and oxygen. Compound (1) and its use has been described, inter alia, in U.S. Pat. Nos. 4,812,498, 4,948,666, 4,681,905, and its preparation in U.S. Pat. Nos. 5,229,521 and 4,812,498; compound (14) is particularly effective as UV absorber and its preparation is described, inter alia, in U.S. Pat. Nos. 4,001,266, 4,041,044, 4,219,480, 4,230,867 and 4,999,433; the known α-modification of compound (14) has, in pure form, a melting point of about 156° C. and is commercially available under the trade name Tinuvin® 327.

The novel amorphous forms of compound 1–12, 14, and 18 give a line-free X-ray diffraction diagram, e.g. with Cu-kα-radiation. They are also characterised by their glass transition temperature (Tg) which, for example in compound 14, is in the range from 20–30° C., in particular from 20–25° C.

The preparation of the amorphous form of compounds 1–12, 14 and also 18 is conveniently carried out by the novel process or, in particular, by rapidly cooling (chilling) the melt, preferably starting from a temperature of a little above the melting point or higher, typically 1–30° C. above the melting point, to a temperature below the glass transition temperature (Tg), for example 20–50° C. below Tg.

This can be done in known manner, for example by application to a cooled surface (e.g. a cooling conveyer), introduction into a cooled nonreactive liquid or by cooling in a stream of gas, for example with air or nitrogen. The temperature of the solid or liquid cooling medium is preferably below 100° C., in particular below 50° C., for example in the range from 0–50° C., preferably in the range from 5–20° C.; the temperature of the stream of gas used for cooling is preferably 20° C. or lower, for example in the range from 0–20° C., preferably from 0–10° C.

The preparation of the amorphous form of compound 14 is conveniently carried out by rapidly cooling (chilling) a melt of the compound, preferably starting from a temperature of 159° C. or more to a temperature of 20° C. or lower.

This can be done in known manner, for example by application to a cooled surface, introduction into a cooled nonreactive liquid or by cooling in a stream of gas, for example with air or nitrogen. The temperature of the cooling medium is preferably below 20° C., in particular below 10° C., for example in the range from −10 to +15° C., preferably from −5 to +5° C.

The amorphous solid so obtained can be comminuted by known methods, for example by grinding, to any desired particle size, the product temperature conveniently being kept below the glass transition temperature.

The novel amorphous modifications are distinguished over the crystalline modifications by a number of advantages, inter alia, in preparation, further processing and use. Rapidly cooling the melt to below the glass transition temperature, for example, results in the heat of crystallisation not being released (in the case of cmpd. (1) about 85–88 J/g), so that less energy needs to be eliminated by cooling and the cooling time of the oxidation-sensitive products can be reduced. The incorporation and distribution in the material to be stabilised is furthermore facilitated by the lack of heat of fusion. The novel modifications are dissolved more easily and homogeneously in, on the one hand, organic solvents, such as lubrication oils, lubricants, urethanes, prepolymers and others and, on the other hand, in the organic material to be stabilised, for example the organic polymer. Thus it is possible to achieve a more uniform distribution in the substrate, to prevent inhomogeneity as well as to obtain good processability and excellent effectiveness.

In addition, the plastic metastable state of the subcooled melts makes processing in the extruder possible, where either the pure amorphous form can be used or a mixture consisting of the novel amorphous modification and of the customary crystalline form and/or other customary additives.

This invention therefore also relates to a mixture consisting of a subcooled melt or of an amorphous solid of one or several of compounds 1–12, 14, and 18, of a crystalline compound and/or of a customary stabiliser, the proportion of the novel amorphous modification preferably being from 5 to 100% by weight, in particular from 20 to 100% by weight, of the mixture and wherein, in particular, the customary stabiliser can be either solid or also amorphous.

Particularly important are in this connection the amorphous mixtures which usually have the same advantageous application properties as the amorphous single compounds. Many low molecular weight compounds, such as those cited above, are soluble in one another in the melt and are capable of forming eutectic mixtures. In mixtures, the component having the lowest melting point can serve as solvent for one or several other components. Thus it is possible to obtain multicomponent single-phase amorphous mixtures which are distinguished by having only one single glass transition temperature Tg.

Owing to the interaction of the individual compounds, the mixture physically has a novel amorphous structure, the Tg value of which can be derived from the Tg values of the individual amorphous modifications and their concentration. Accordingly, it is possible to selectively prepare single-phase microhomogeneous mixtures by mixing these compounds with one another or by admixing other low molecular weight additives, such as the compounds No. 13, 15, 16, 17 which, as is known, also have an amorphous modification. It is even possible to use some additives which are only known in crystalline form, the Tg of which is far below 15° C. (e.g. compound bis(2,2,6,6-tetramethylpiperidin-4-yl) sebacate) in a small amount. The glass transition temperature can here be adjusted preferably to between 40 and 100° C. by skilful combination of the compounds to warrant on the one hand an amorphous stabiliser which melts easily and at low temperature (energetically favourable, advantageous for certain applications) and, on the other hand, good storage stability.

Novel Crystalline Modification of Compound No. 14

It has furthermore been found that a novel crystal modification (β-form; high-temperature modification) can be obtained by equilibrating 2-(2-hydroxy-3,5-di-tert-butylphenyl)-5-chlorobenzotriazole (compound No. 14) in a specific temperature range. This crystal modification is distinguished over the conventional α-crystalline form by enhanced performance properties, such as higher bulk density and compacted bulk density, flowability, improved dispersibility in the substrate and less evolution of dust when handled and this modification also constitutes an object of this invention.

The physical properties of the novel β-modifications of compound 14 have a number of differences as compared to the α-modification, some of which have been found to be as follows:

|  | α-modification | β-modification |
|---|---|---|
| melting point | 156° C. | 158° C. |
| contact angle of benzyl alcohol | 24.5° | 19.5° |
| loose bulk density | 0.39 kg/l | 0.49 kg/l |
| compacted bulk density | 0.72 kg/l | 0.79 kg/l |
| compressibility | 46% | 38% |
| angle of repose | 54° | 50° |
| flow factor (acc. to Jenike) | 1.6 | 2.6 |

The following Table provides the interplanar spacings determined by X-ray diffraction (Cu-kα-radiation; measurement of the powder diagrams in transmission geometry using a Guinier camera) for the known α-form as well as for the novel β-crystalline form (d, given in Å=$10^{-10}$ m) and reflection intensities (visually determined):

| α-modification | | β-modification | |
|---|---|---|---|
| d [Å] | intensity | d [Å] | intensity |
| 16.0 | medium | 16.1 | weak |
| 9.8 | strong | 9.4 | strong |
| 8.6 | very weak | 8.0 | very strong |
| 8.0 | very strong | 7.2 | weak |
| 6.4 | weak | 5.88 | weak |
| 5.99 | medium | 5.61 | medium |
| 5.61 | weak | 5.42 | weak |
| 5.43 | weak | 5.37 | weak |
| 5.07 | very weak | 5.22 | very weak |
| 4.83 | strong | 4.84 | strong |
| 4.58 | strong | 4.69 | strong |
| 4.55 | strong | 4.49 | medium |
| 4.30 | weak | 4.18 | very weak |
| 4.04 | very weak | 4.15 | very weak |
| 3.99 | strong | 3.94 | very strong |
| 3.87 | very strong | 3.79 | medium |
| 3.71 | very weak | 3.63 | very weak |
| 3.63 | very weak | 3.62 | very weak |
| 3.20 | very weak | 3.43 | very weak |
| 3.13 | medium | 3.34 | very weak |
| 3.10 | very weak | 3.23 | medium |
| 3.04 | weak | 3.20 | very weak |
| 2.94 | medium | 3.09 | very weak |
| 2.90 | very weak | 3.03 | medium |
|  |  | 2.92 | weak |

Characteristic of the β-form are, for example, the reflexes corresponding to the interplanar spacings (d) at $d=9.4 \cdot 10^{-10}$ m; at $d=4.69 \cdot 10^{-10}$ m; $d=3.94 \cdot 10^{-10}$ m and $d=3.79 \cdot 10^{-10}$ m (high or medium intensity).

The inventive modification of compound 14 can be obtained by equilibrating the compound at a temperature of above 70° C., preferably above 95° C., more preferably above 106° C., and then cooling it rapidly, preferably to 15–20° C. or lower. Suitable for equilibration are, for example, tempering as well as dissolving and/or melting processes with mixing, for example during the extrusion in the novel process. Crystallisation prior to the cooling process gives the β-crystalline form, the amorphous form being obtained otherwise.

The preparation of the β-crystalline form is conveniently carried out by crystallising compound 14 above 70° C., typically above 95–106° C., preferably above 106° C., or by tempering the α-crystalline form in the temperature range from 70° C., preferably from 95° C., most preferably from 106° C., and at a melting point of the α-crystalline form; i.e. typically in the range from 106° C. to 155° C., preferably from 110C. to 150° C., with subsequent rapid cooling of the β-crystalline form obtained typically to 50° C. or lower, preferably to 15–30° C. or room temperature (20–25° C.) or lower.

Crystallisation can be carried out by the customary methods of the art, for example by crystallisation from a solution or subcooled melt of compound which is kept below the melting point, or by cooling a melt.

The cooling process from a temperature of above 70° C., such as above 95–106° C. or above 156° C., to 50° C. or room temperature can proceed continuously or discontinuously, the cooling rate being slowed or stopped in the range from 95 to 156° C., preferably from 106–150° C. The cooling process can usefully also be combined with the moulding of the product, e.g. granulation or pastillation. Typical examples of concrete processes are fluid bed granulation or prilling.

For tempering, the compound is heated either direct or with addition of a suitable solvent, e.g. xylene, toluene or a mixture of xylene and butanol with a sufficiently high boiling point, conveniently for about 20 minutes to 24 hours to a temperature in the cited range. Cooling is then carried out as indicated above.

Suitable solvents are, for example, those having a boiling point which is markedly higher than 95° C., in particular higher than 106° C., at normal pressure, preferably alcohols or hydrocarbons, such as toluene, xylene or mesitylene or their mixtures. The use of solvents having lower boiling points is also possible, in which case the pressure is usefully increased such that the solvent remains liquid in the cited temperature range. Such solvents can subsequently be removed more easily than the high-boiling solvents mentioned at the outset.

When using a solvent, compound 14 can also be dissolved completely or partially, and the crystallisation of the dissolved components can then be achieved, inter alia, by gentle cooling to the lower range of the cited temperature range, for example to 70–100° C., 95–110° C. or 106–120° C., and/or by removing the solvent by distillation.

The β-crystalline product can, if required, be brought into any other desired form of presentation and particle size by known methods, such as grinding, compressing, extruding or granulating.

The use of mixtures of the novel modifications with one another and with the customary α-crystalline modification has also advantages of the cited kind over the use of the pure α-crystalline modification. The novel mixture consisting of different modifications of compound 14 preferably contains at least 40% by weight, preferably at least 60% by weight, more preferably at least 80% by weight, of β-crystalline and/or amorphous form and not more than 50% by weight, preferably not more than 20% by weight, more preferably not more than 10% by weight, of foreign components (each based on the total weight of the mixture).

Another advantage of the novel β-modification of compound 14 consists in the easier and more homogeneous solubility in, on the one hand, organic solvents, such as lubrication oils, lubricants, urethanes, prepolymers and others and, on the other hand, in the organic material to be stabilised, for example the organic polymer, such that a more uniform distribution is achieved therein, inhomogeneity is prevented and excellent effectiveness is warranted.

The novel modifications of compound 14 are particularly suitable for stabilising organic materials, for example in particular the organic polymers cited hereinbelow, against damage by light, oxygen or heat. The novel modifications are very particularly suitable as light stabilisers (UV absorbers).

Colour-stabilisation of Compound No. 13

Amorphous pentaerythritol-tetrakis(3-[3',5'-di-tert-butyl-4'-hydroxyphenyl]propionate) (CAS reg. No. 006683-19-8; compound No. 13), which is usually obtained as a colourless powder during synthesis, quickly darkens during storage, the product taking on a greenish to yellow hue (greening). Depending on the storage conditions, in particular on exposure to light and oxygen, this unwanted effect occurs usually after about 4–12 weeks.

The use of mixtures comprising this compound in the novel extrusion process surprisingly shows that in the case of certain additives the colour stability of the amorphous compound 13 is markedly improved and the greening effect is prevented or at least slowed down very much. It is important in this connection that a microhomogeneous amorphous mixture is obtained.

In another of its aspects, this invention therefore also relates to a process for stabilising the colour of amorphous pentaerythritol-tetrakis(3-[3',5'-di-tert-butyl-4'-hydroxyphenyl]propionate), which comprises admixing a stabiliser of the class consisting of the organic phosphites, phosphonites and/or benzofuran-2-ones to a melt of pentaerythritol-tetrakis(3-[3',5'-di-tert-butyl-4'-hydroxyphenyl]propionate) and rapidly cooling the mixture so obtained.

The use of a stabiliser of the class consisting of the organic phosphites, phosphonites and/or benzofuran-2-ones for stabilising the colour of amorphous pentaerythritol-tetrakis(3-[3',5'-di-tert-butyl-4'-hydroxyphenyl]propionate) is another object of this invention.

The compound No. 13 colour-stabilised in this manner forms a microhomogeneous phase together with the stabiliser. The stabiliser component (organic phosphite, phosphonite and/or benzofuran-2-one) in this phase is preferably at least 1% by weight, typically 1–95% by weight, in particular 5–90% by weight, more preferably 5 to 55% by weight.

The cooling process which gives the partially amorphous or, preferably, single-phase amorphous colour-stabilised compound No. 13 can be carried out in the manner described above for the preparation of the novel amorphous modifications.

In this connection, phosphites or organic phosphites will be understood as meaning the compounds of formula P(OR)$_3$, wherein the radicals R are hydrocarbon radicals which may contain hetero atoms, and where a maximum of two of the three radicals R may additionally be hydrogen atoms. Hetero atoms are all atoms with the exception of carbon and hydrogen, in particular the N, O, F, Si, P, S, Cl, Br, Sn and I atoms.

Phosphonites are esters of the phosphonous acid of formula P(OR)$_2$R, wherein R has the meanings given above or may be halogen.

Phosphites or phosphinites preferably used in the inventive process are those, which correspond to one of formulae (1) to (7), (1) R'$_1$—Y'—P(OR'$_2$)(OR'$_3$), (2) A'—(X'—P(OR'$_2$)(OR'$_3$))$_{n'}$, (3) [structure with R'$_7$, R'$_8$, P, O, A']$_q$ (4) [structure with D', P, O, R'$_1$, CH$_3$]$_p$ (5) R'$_1$—O—P(structure)P—O—R'$_1$, (6) [structure with R'$_{14}$, R'$_{15}$, E', P, Z']$_y$ (7) [structure with P, Q', R'$_{16}$]$_{y-1,z}$ wherein the indices are integers, and
n' is 2, 3 or 4; p is 1 or 2; q is 2 or 3; r is 4 to 12; y is 1, 2 or 3; and z is 1 to 6;

A', if n' or q is 2, is alkylene of 2 to 18 carbon atoms; alkylene of 2 to 12 carbon atoms which is interrupted by —S—, —O— or —NR'$_4$—; a radical of one of formula

[structures with R'$_5$, R'$_6$, B'] or

[cyclohexyl structure with B']

or phenylene;

A', if n' or q is 3, is a radical of formula —C$_r$H$_{2r-1}$—;
A', if n' is 4, is the radical of formula C(CH$_2$)$_4$;
A" has the meaning of A', if n' is 2;
B' is a radical of formula —CH$_2$—; —CHR'$_4$—; —CR'$_1$R'$_4$—; —S— or a direct bond; or C$_5$–C$_7$cycloalkylidene; or cyclohexylidene which is substituted by 1 to 4 C$_1$–C$_4$alkyl radicals in position 3, 4 and/or 5;
D', if p is 1, is methyl and, if p is 2, is —CH$_2$OCH$_2$—;
E', if y is 1, is alkyl containing 1 to 18 carbon atoms, a radical of formula —OR', or halogen;
E', if y is 2, is a radical of formula —O—A"—O—;
E', if y is 3, is a radical of formula R'$_4$—C(CH$_2$O)$_3$—;
Q' is the radical of an at least z-valent alcohol or phenol, which radical is bound via the alcoholic or phenolic O-atom (s) to the P-atom(s);
R'$_1$, R'$_2$ and R'$_3$ are each independently of one another alkyl containing 1 to 30 carbon atoms; alkyl containing 1 to 18 carbon atoms, which is substituted by halogen, —COOR'$_4$, —CN or —CONR'$_4$R'$_4$; alkyl containing 2 to 18 carbon atoms, which is interrupted by —S—, —O— or —NR'$_4$—; phenyl-C$_1$–C$_4$alkyl; cycloalkyl containing 5 to 12 carbon atoms; phenyl or naphthyl; phenyl or naphthyl, each of which is substituted by halogen, 1 to 3 alkyl radicals or alkoxy radicals containing a total of 1 to 18 carbon atoms or by phenyl-$C_1$-$C_4$alkyl; or a radical of formula

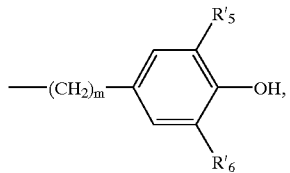

wherein m is an integer from the range of 3 to 6;

$R'_4$, or the radicals $R_4'$, are each independently of one another hydrogen; alkyl containing 1 to 18 carbon atoms; cycloalkyl containing 5 to 12 carbon atoms; or phenylalkyl containing 1 to 4 carbon atoms in the alkyl moiety;

$R'_5$ and $R'_6$ are each independently of the other hydrogen; alkyl containing 1 to 8 carbon atoms, or cycloalkyl containing 5 or 6 carbon atoms;

$R'_7$ and $R'_8$, where q=2, are each independently of the other $C_1$–$C_4$alkyl or are together a 2,3-dehydropentamethylene radical; and $R'_7$ and $R'_8$, where q=3, are methyl;

the substituents $R'_{14}$ are each independently of one another hydrogen; alkyl containing 1 to 9 carbon atoms or cyclohexyl;

the substituents $R'_{15}$ are each independently of one another hydrogen or methyl; and $R'_{16}$ is hydrogen or $C_1$–$C_4$alkyl, and in the case where several radicals $R'_{16}$ are present, the radicals $R'_{16}$ are identical or different;

X' and Y' are each a direct bond or —O—; and

Z' is a direct bond; —$CH_2$—; —$C(R'_{16})_2$— or —S—.

A particularly preferred process is that, wherein the phosphite or phosphonite is one of formula (1), (2), (5) or (6), wherein n' is the number 2, and y is the number 1 or 2;

A' is alkylene containing 2 to 18 carbon atoms; p-phenylene or p-biphenylene;

E', where y=1, is $C_1$–$C_{18}$alkyl, —$OR_1$ or fluoro; and where y=2, is p-biphenylene;

$R'_1$, $R'_2$ and $R'_3$ are each independently of one another alkyl containing 1 to 18 carbon atoms; phenyl-$C_1$–$C_4$alkyl; cyclohexyl; phenyl; phenyl which is substituted by 1 to 3 alkyl radicals containing a total of 1 to 18 carbon atoms;

the substituents $R'_{14}$ are each independently of one another hydrogen or alkyl containing 1 to 9 carbon atoms;

$R'_{15}$ is hydrogen or methyl;

X' is a direct bond;

Y' is —O—; and

Z' is a direct bond or —$CH(R'_{16})$—.

Of particular technical interest are those phosphites or phosphonites which are listed hereinafter in the list of possible costabilisers under item 4.

In the novel process those benzofuran-2-ones are preferably used, which correspond to formula (8)

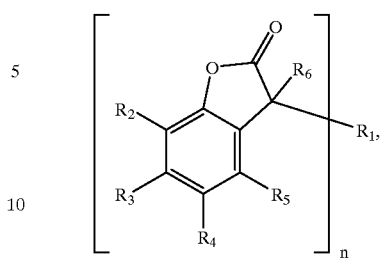

wherein, if n is 1, $R_1$ is naphthyl, phenanthryl, anthryl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by $C_1$–$C_4$alkyl, $C_1$–$C_4$alkoxy, $C_1$–$C_4$alkylthio, hydroxy, halogen, amino, $C_1$–$C_4$alkylamino, phenylamino or di($C_1$–$C_4$alkyl)amino, or $R_1$ is a radical of formula 9

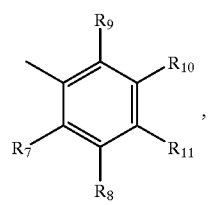

and if n is 2, $R_1$ is unsubstituted or $C_1$–$C_4$alkyl- or hydroxy-substituted phenylene or naphthylene; or —$R_{12}$—X—$R_{13}$—, $R_2$, $R_3$, $R_4$ and $R_5$ are each independently of one another hydrogen, chloro, hydroxy, $C_1$–$C_{25}$-alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$-alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulfur or

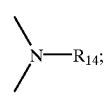

$C_6$–$C_9$cycloalkylcarbonyloxy, benzoyloxy or $C_1$–$C_{12}$alkyl-substituted benzoyloxy; or $R_2$ and $R_3$, or $R_3$ and $R_4$, or $R_4$ and $R_5$, together with the linking carbon atoms, are a benzene ring, $R_4$ is additionally —$(CH_2)_p$—$COR_{15}$ or —$(CH_2)_q$OH or, if $R_3$, $R_5$ and $R_6$ are hydrogen, $R_4$ is additionally a radical of formula 10

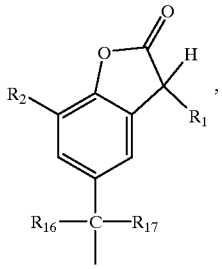
(10)

wherein $R_1$ is as defined above for n=1, $R_6$ is hydrogen or a radical of formula 11

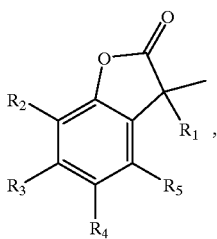
(11)

wherein $R_4$ is not a radical of formula 10 and $R_1$ is as defined above for n=1, $R_7$, $R_8$, $R_9$, $R_{10}$ and $R_{11}$ are each independently of one another hydrogen, halogen, hydroxy, $C_1$–$C_{25}$alkyl; $C_2$–$C_{25}$alkyl which is interrupted by oxygen, sulfur or

$C_1$–$C_{25}$alkoxy; $C_2$–$C_{25}$alkoxy which is interrupted by oxygen, sulfur or

$C_1$–$C_{25}$alkylthio, $C_3$–$C_{25}$-alkenyl, $C_3$–$C_{25}$alkenyloxy, $C_3$–$C_{25}$alkynyl, $C_3$–$C_{25}$alkynyloxy, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; $C_1$–$C_4$alkylamino, di($C_1$–$C_4$alkyl) amino, $C_1$–$C_{25}$alkanoyl; $C_3$–$C_{25}$alkanoyl which is interrupted by oxygen, sulfur or

$C_1$–$C_{25}$alkanoyloxy; $C_3$–$C_{25}$alkanoyloxy which is interrupted by oxygen, sulfur or

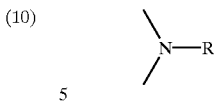

$C_1$–$C_{25}$alkanoylamino, $C_3$–$C_{25}$alkenoyl; $C_3$–$C_{25}$alkenoyl which is interrupted by oxygen, sulfur or

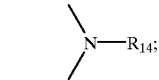

$C_3$–$C_{25}$-alkenoyloxy; $C_3$–$C_{25}$alkenoyloxy which is interrupted by oxygen, sulfur or

$C_6$–$C_9$-cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

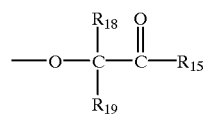

or

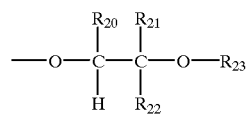

or also, in formula 9, $R_7$ and $R_8$, or $R_8$ and $R_{11}$, together with the linking carbon atoms, are a benzene ring, $R_{12}$ and $R_{13}$ are each independently of the other unsubstituted or $C_1$–$C_4$alkyl-substituted phenylene or naphthylene, $R_{14}$ is hydrogen or $C_1$–$C_8$alkyl, $R_5$ is hydroxy,

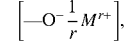

$C_1$–$C_{18}$alkoxy or

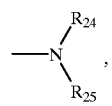

$R_{16}$ and $R_{17}$ are each independently of the other hydrogen, $CF_3$, $C_1$–$C_{12}$alkyl or phenyl, or $R_{16}$ and $R_{17}$, together with the linking carbon atom, are a $C_5$–$C_8$cycloalkylidene ring which is unsubstituted or substituted by 1 to 3 $C_1$–$C_4$alkyl;

$R_{18}$ and $R_{19}$ are each independently of the other hydrogen, $C_1$–$C_4$alkyl or phenyl, $R_{20}$ is hydrogen or $C_1$–$C_4$alkyl, $R_{21}$ is hydrogen, unsubstituted or $C_1$–$C_4$alkyl-substituted phenyl; $C_1$–$C_{25}$alkyl; $C_2$–$C_{25}$alkyl which is interrupted by oxygen, sulfur or

$C_7$–$C_9$phenylalkyl which is unsubstituted or substituted at the phenyl radical by 1 to 3 $C_1$–$C_4$alkyl; $C_7$–$C_{25}$phenylalkyl which is interrupted by oxygen, sulfur or

which is unsubstituted or substituted at the phenyl radical by 1 to 3 $C_1$–$C_4$alkyl, or $R_{20}$ and $R_{21}$, together with the linking carbon atoms, are a $C_5$–$C_{12}$cycloalkylene ring which is unsubstituted or substituted by 1 to 3 $C_1$–$C_4$alkyl;

$R_{22}$ is hydrogen or $C_1$–$C_4$alkyl, $R_{23}$ is hydrogen, $C_1$–$C_{25}$alkanoyl, $C_3$–$C_{25}$alkenoyl; $C_3$–$C_{25}$alkanoyl which is interrupted by oxygen, sulfur or

$C_2$–$C_{25}$alkanoyl which is substituted by a di($C_1$–$C_6$alkyl) phosphonate group; $C_6$–$C_9$cycloalkylcarbonyl, thenoyl, furoyl, benzoyl or $C_1$–$C_{12}$alkyl-substituted benzoyl;

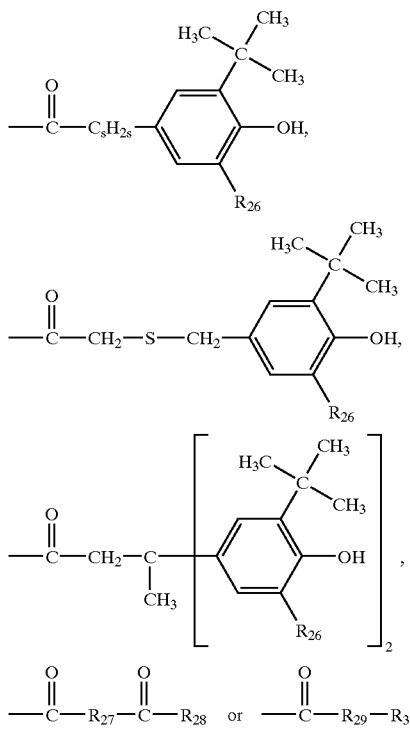

$R_{24}$ and $R_{25}$ are each independently of the other hydrogen or $C_1$–$C_{18}$alkyl, $R_{26}$ is hydrogen or $C_1$–$C_8$alkyl, $R_{27}$ is a direct bond, $C_1$–$C_{18}$alkylene; $C_2$–$C_{18}$alkylene which is interrupted by oxygen, sulfur or

$C_2$–$C_{18}$alkenylene, $C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

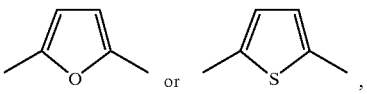

$R_{28}$ is hydroxy,

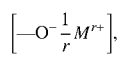

$C_1$–$C_{18}$alkoxy or

$R_{29}$ is oxygen, —NH— or

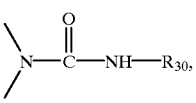

$R_{30}$ is $C_1$–$C_{18}$alkyl or phenyl,
$R_{31}$ is hydrogen or $C_1$–$C_{18}$alkyl,
M is an r-valent metal cation,
X is a direct bond, oxygen, sulfur or —$NR_{31}$—,
n is 1 or 2,
p is 0, 1 or 2,
q is 1, 2, 3, 4, 5 or 6,
r is 1, 2 or 3, and
s is 0, 1 or 2.

Benzofuran-2-ones of particular technical interest are those which are listed hereinafter in the list of possible costabilisers under item 14.

Furthermore, this invention relates to a composition, which comprises a) pentaerythritol-tetrakis(3-[3',5'-di-tert-butyl-4'-hydroxyphenyl]propionate), and b) at least one compound of the benzofuran-2-one type.

The novel compositions contain pentaerythritol-tetrakis(3-[3',5'-di-tert-butyl-4'-hydroxyphenyl]propionate) (component a) preferably in amorphous form. Particularly preferred compositions are those, which comprise components a and b side by side in the same amorphous phase. The inventive stabiliser compositions usually contain less than 10% by weight of high molecular weight or polymeric components, typically those having a molecular weight of 1500 g/mol or higher; there are mostly no such high molecular weight components present.

Use as Stabiliser for Organic Material

The products of the process of this invention, the novel amorphous compounds, the colour-stabilised compound 13 according to this invention, and also the novel β-crystalline modification of compound 14 are particularly suitable for stabilising organic materials against damage by light, oxygen or heat.

The materials to be stabilised may be, for example, oils, fats, paint systems, cosmetics, photographic materials or biocides. Particularly interesting is the use in polymeric materials, as is the case in plastics, rubbers, coating materials, photographic material or sizes. When used in cosmetic preparations, the material to be protected is often not the preparation itself, but the skin or hair to which the preparation is applied.

Illustrative examples of polymers and other substrates which can be stabilised in this manner are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

This invention therefore also relates to a composition, which comprises

A) an organic material susceptible to oxidative, thermal or/and actinic degradation or build-up, and B) the amorphous form of one of the compounds No. 1–12, 14, 18, the colour-stabilised amorphous compound 13 and/or the β-crystalline form of the compound 14 as stabiliser, as well as to the use of the amorphous form of one of the compounds No. 1–12, 14, 18, of the colour-stabilised amorphous compound 13 and/or of the β-crystalline form of compound 14 for stabilising organic material against oxidative, thermal or actinic degradation or build-up.

Component B is preferably the amorphous form of one of the compounds No. 1–12, 14, 18 and also the β-crystalline form of compound 14.

The invention also relates to a process for stabilising organic material against thermal, oxidative or/and actinic degradation or build-up, which comprises applying the amorphous form of one of the compounds No. 1–12, 14, 18, the colour-stabilised amorphous compound 13 and/or the β-crystalline form of compound 14 to this material and/or preferably adding them thereto, as well as to the corresponding use. The amorphous form of one of the compounds No. 1–12, 14, 18, the colour-stabilised amorphous compound 13 and/or the β-crystalline form of compound 14 can be used here by itself or as component of a mixture of the amorphous form of one or several compounds No. 1–12, 14, 18, of the colour-stabilised amorphous compound 13 and/or of the β-crystalline form of compound 14 with the conventional crystalline form and/or other conventional additives.

The amount of the stabiliser (amorphous and, if required, crystalline) to be used in total depends on the organic material to be stabilised and on the intended use of the stabilised material. The novel composition generally comprises, per 100 parts by weight of component A, 0.01 to 15, preferably 0.05 to 10 and, more preferably, 0.1 to 5, parts by weight of the novel stabiliser (novel amorphous modification of one of the compounds No. 1–12, 14, 18, colour-stabilised amorphous compound 13 and/or β-crystalline form of compound 14 or mixture comprising a novel amorphous or β-crystalline modification).

Particularly interesting is the use of the novel stabiliser in synthetic organic polymers as well as corresponding compositions, in particular thermoplastic polymers which are processed at elevated temperatures, for example by extruding, blow moulding, calendering, injection moulding, casting, compressing, sintering, spinning, foaming, soldering, laminating, heat-moulding, and the like.

The organic materials to be protected are preferably natural, semi-synthetic or synthetic organic materials.

The novel stabiliser can be used particularly advantageously in compositions which comprise as component A a synthetic organic polymer, preferably a thermoplastic polymer or a binder for coatings, such as paint systems. Suitable thermoplastic polymers are, for example, polyolefins, preferably polyethylene (PE) and polypropylene (PP), as well as those polymers which contain hetero atoms in the main chain.

In a preferred aspect, this invention also relates to a composition wherein the novel modification is incorporated in a thermoplastic polymer, in a paint binder, in particular one based on an acrylic, alkyd, polyurethane, polyester or polyamide resin or corresponding modified resins, or in a photographic material. The material to be protected (component A) can in this case be a thermoplastic polymer, a paint binder, in particular based on an acrylic, alkyd, polyurethane, polyester or polyamide resin or corresponding modified resins, a photographic material, or a colourant present in this material.

Particularly interesting is also the use of the novel modifications as stabiliser for coatings, for example for paint systems.

The incorporation in the materials to be stabilised can, for example, be carried out by admixing or applying the novel stabiliser and, if required, other additives, by the customary methods of the art. In the case of polymers, in particular of synthetic polymers, the incorporation can be carried out before or after moulding, or by applying the dissolved or dispersed compound to the polymer, if required with subsequent evaporation of the solvent. Elastomers can also be stabilised as latices. Another possibility of incorporating the novel stabiliser in polymers consists in their addition before, during or immediately after the polymerisation of the corresponding monomers or before crosslinking. The amorphous or β-crystalline compound can in this case be added as such or also in encapsulated form (e.g. in waxes, oils or polymers). If the stabiliser is added before or during the polymerisation, it can also serve as chain length regulator (chain terminator) for the polymers.

The novel stabiliser can also be added to the plastics to be stabilised in the form of a master-batch which comprises the stabiliser e.g. in a concentration of 2.5 to 25% by weight.

The incorporation of the novel stabiliser may conveniently be carried out by the following methods:

- as emulsion or dispersion (e.g. to latices or emulsion polymers),
- as dry mixture before mixing additive components or polymer mixtures,
- by direct addition to the processing apparatus (e.g. extruder, internal mixer, etc.)
- as solution or melt.

The novel stabiliser is preferably added to the polymer before or after processing, preferably as dry mixture during the mixing of additive components or polymer mixtures, or by direct addition to the processsing apparatus.

Polymer compositions of this invention can be used in different form or can be processed to different products, e.g. foils, fibres, filaments, moulding compositions, profiles, or binders for paint systems, sizes or putties.

In addition to the novel stabiliser, the novel compositions can comprise as additional component (C) one or several conventional additives, such as antioxidants, further light stabilisers, metal deactivators, phosphites or phosphonites. Illustrative examples thereof are:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, ε-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)- malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

11.17. Amides of β-(3,5-di-tert-butyl-4-hydroxylphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl- 2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotrazole, 2-(3',5'-bis-(α,α-dimethylbenzyl)-2'- hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504–96–6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanlide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

Especially preferred are the following phosphites:
Tris(2,4di-tert-butylphenyl) phosphite (Irgafos® 168, Ciba-Geigy), tris(nonylphenyl) phosphite, (A)

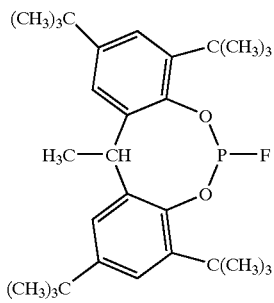

(B)

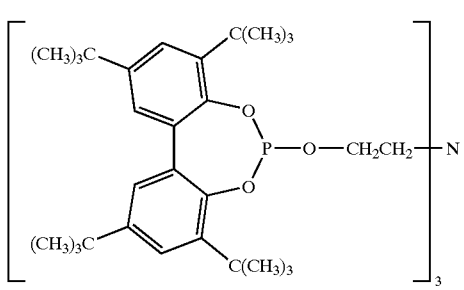

(C)

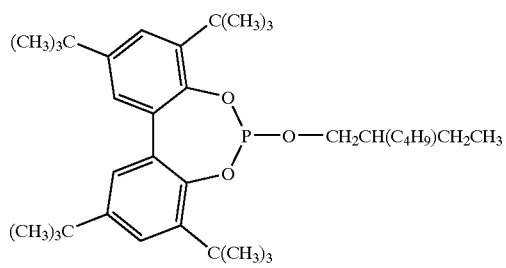

(D)

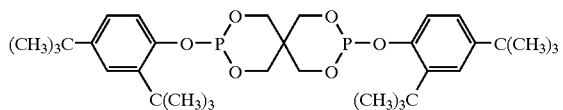

(E)

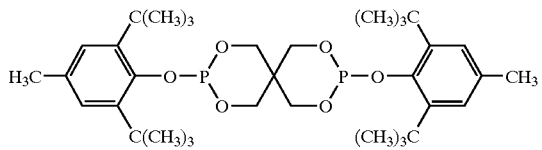

(F)

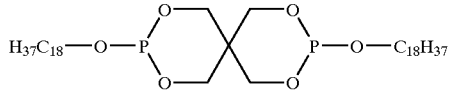

(G)

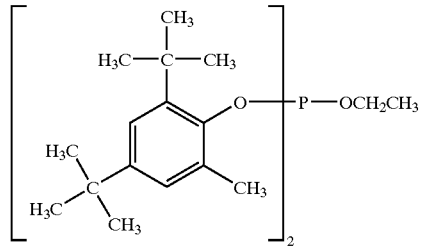

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dhexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zink pyrocatecholate.

11. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3, 5-dimethylphenyl)-5,7-di-tert-butyl-benzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The type and amount of the further stabilisers added is determined by the type of substrate to be stabilised and by its envisaged use; often, 0.0005–10, for example 0.001–5, preferably 0.01–2.5%, by weight, based on the material to be stabilised, are added.

It is particularly advantageous to use the novel modifications of compounds No. 1, 10, 11 and/or 14 in combination with sterically hindered amines, for example 2,2,6,6-tetralkylpiperidine derivatives. This invention therefore relates to a synergistic stabiliser mixture, which comprises (a) the β-crystalline modification of compound 14 and/or the amorphous modification of compound No. 1, 10, 11, and/or 14, and (b) at least one sterically hindered amine, the salt thereof with any acid or the complex thereof with a metal, as well as to a composition, which comprises A) an organic material susceptible to oxidative, thermal or/and actinic degradation or build-up, B) the β-crystalline modification of compound 14 and/or the amorphous modification of compound No. 1, 10, 11, and/or 14, and also C) a conventional additive of the sterically hindered amine type.

Preferred sterically hindered amines are, for example, those which are given in the above list under item 2.6.

It is also particularly advantageous to use the novel modifications in combination with costabilisers of the 2-(2-hydroxyphenyl)-1,3,5-triazine type, as exemplified in the above list under item 2.8.

The invention is illustrated by the following Examples. In the Examples as well as in the remaining description and in the patent claims, all parts or percentages are by weight, unless otherwise stated. The temperatures are determined by differential thermoanalysis [DSC] at a heating rate of 4° C./min (m.p.) or 20° C./min ($T_G$), unless otherwise stated.

In the Examples, compound A is bis(2,2,6,6-tetramethylpiperidin-4-yl)sebacate. In the Examples, compound B is a commercially available mixture of different phosphonites (CAS-no. 119345-01-6) having the main components

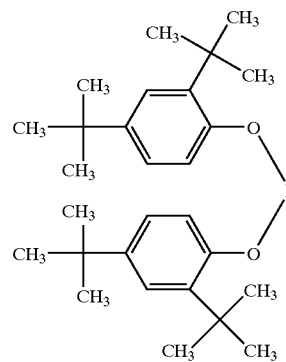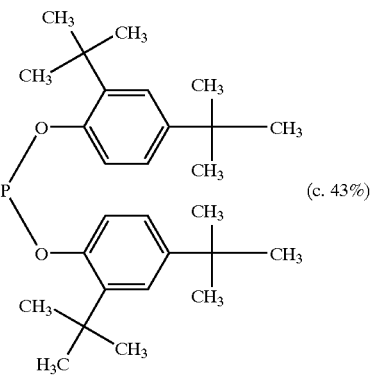

(c. 43%)

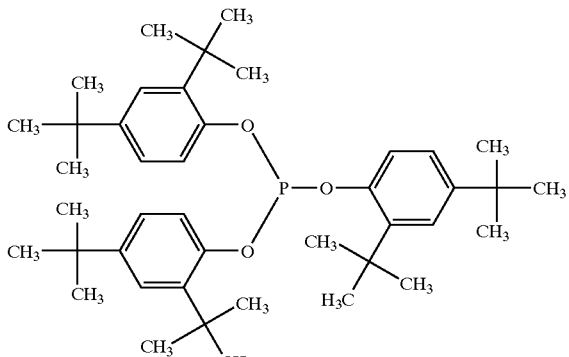

(ca. 17%)

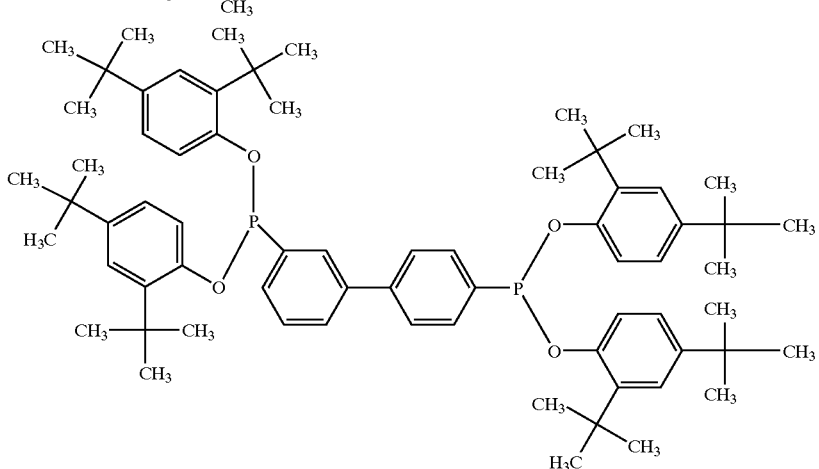

(c. 17%)

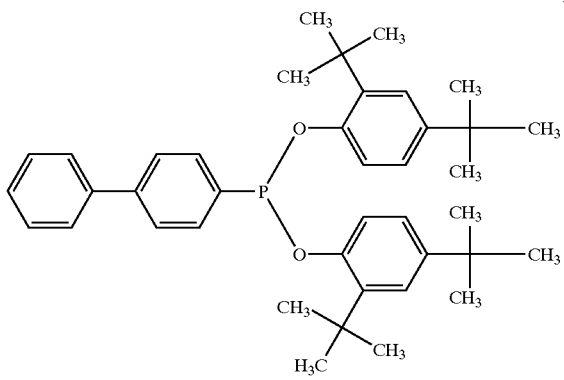

(c. 13%)

The following abbreviations are used in the Examples and Tables:

DSC: differential scanning calorimetry (quantitative dynamic differential thermoanalysis)

Tg or $T_G$ glass transition temperature (DSC, +20° C./min)

h, min: hour(s), minute(s)

m.p. melting point (DSC, +4° C./min)

EXAMPLE 1

Preparation of the Amorphous Form of Compound No. 1 on Laboratory Scale

A 30 ml boiling glass is charged with 10 g of crystalline powdered 2,2'-methylenebis(4-[1,1,3,3-tetramethylbutyl]-6-benzotriazol-2-yl-phenol) (compound No. 1) which is heated under nitrogen indirectly via spoon sieve and controllable hot blast (air temperature 235–245° C.). At 200° C., the powder turns into a pale yellow, clear and low viscous melt which is tempered at 205° C.

After pouring the melt in portions on a stainless steel plate cooled to 15° C. with water, the melt quickly becomes highly viscous and solidifies spontaneously. Pellets are prepared from part of the melt by dripping on the cooled steel plate. The vitreous composition can be easily separated from the cooling plate and pulverised in a mortar. DSC (heating rate 20° C./min.) confirms the amorphous structure, $T_g$=72–75° C.

EXAMPLE 1a

Preparation of the Amorphous Form of Compounds 1–12, 18, 19 on Laboratory Scale

As described in Example 1, a 30 ml boiling glass is charged with 10 g each of crystalline powdered compound which is heated under nitrogen indirectly via spoon sieve and controllable hot blast. At T> melting point (m.p.), the powder turns into a colourless or very slightly coloured clear and low viscous melt which is tempered at Ti.

After pouring the melt in portions on a stainless steel plate cooled to Tw with water, the melt quickly becomes highly viscous and solidifies spontaneously. Pellets are formed from part of the melt by dripping on the cooled steel plate. The vitreous composition can be easily separated from the cooling plate and, if desired, can be powdered at T<Tg in a mortar.

The following Table provides molecular weight, melting point (m.p.) of the crystalline form and glass transition temperature (Tg; Cp-leap according to DSC) of the amorphous form:

| No. | molec. weight g/mol | m.p. °C. | Ti °C. | Tw °C. | Tg °C. (+ 20° C./min) |
|---|---|---|---|---|---|
| 1) | 658 | 197 | 205 | 15 | 73–74 |
| 2) | 358 | 161 | 185 | 15 | 30–31 |
| 3) | 594.8 | 177 | 190 | 15 | 59–60 |
| 4) | 636.9 | 160 | 185 | 15 | 54–55 |
| 5) | 775 | 179; 243 | 250 | 15 | 97–98 |
| 6) | 784 | 220 | 225 | 15 | 109–110 |
| 7) | 553 | 200; 221 | 225 | 15 | 69–70 |
| 8) | 699 | 158 | 170 | 15 | 115–120 |
| 9) | 685 | 148 | 165 | 15 | 44–45 |
| 10) | 447.6 | 139 | 160 | 10 | 41–42 |
| 11) | 323.4 | 154 | 170 | 5 | 19–20 |
| 12) | 350.5 | 132 | 145 | 10 | 24–25 |
| 18) | 552 | 163 | 170 | 10 | 52–55 |
| 19) | 441.4 | 113 | 120 | 15 | 33–34 |

The novel amorphous modifications of the above compounds give a linefree X-ray diffraction diagram with Cu-kα-radiation. The novel amorphous form is solid below $T_G$ and plastic above $T_G$.

Typical data for the viscosity of the plastic amorphous form at 130° C. and of the known melt of compound (1) (liquid state, 200° C.) at different shearing speeds D are found in the following Table; the data have been determined using a rotary viscosimeter of the type Rheomat-30/Rheotemp, measuring system cone and plate.

Tab.: Viscosity (Pa·s) of cmpd.(1) in the plastic state (130° C.) and in the liquid state (200° C.)

|  | $D = 1\ s^{-1}$ | $D = 3\ s^{-1}$ | $D = 60\ s^{-1}$ |
|---|---|---|---|
| plastic | 40 | 40 | 20 |
| liquid |  | 0.4 | 0.13 |

EXAMPLE 2

Preparation of Amorphous Pellets

The melt of compound No. 1 is dripped at 200–205° C. and at 20 kg/h throughput via a device of the type SANDVIK-Rotoformer® (feed width 0.25 m) and is pelletised on a 4.5 m long cooling conveyor tempered to 15–25° C. with water. The required cooling time is varied in the range from 8 s to 60 s via the conveyor speed; the drop diameter is 1 mm (8 s cooling time) to 4 mm (60 s cooling time).

Amorphous pellets are obtained which have the properties described in Example 1.

EXAMPLE 2a

A melt of one of the compounds 2, 3, 4, 5, 6, 7, 8, 9, 18 or 19 each is processed by the method described in Example 2. Amorphous pellets are obtained having the properties described in Example 1a.

EXAMPLE 3

Use of Compound (1) in the Novel Extrusion Process 2,2'-Methylenebis(4-[1,1,3,3-tetramethylbutyl]-6-benzotriazol-2-yl-phenol) is added gravimetrically in powdered form at a throughput of 19 kg/h to a laboratory twin-screw extruder (Bühler, Typ DNDL 44). The screw diameter is 44 mm, the ratio length/diameter (l/D) is 40 at 10 barrels, rotational speed of the screw 130 min$^{-1}$.

The laboratory extruder is heated as follows:

barrel 1 (powder addition): cooling water (15° C.), barrels 2/3/4: oil at 205° C., barrels 5/6/7: oil at 210° C., barrels 8/9/10: hydraulic water at 120° C.

Under these conditions, the powder is melted to about 70% up to barrel 7. The paste which is initially low viscous cools quickly to 130° C. from barrel 8 onwards (subcooled melt component about 30%). At a dynamic pressure of 11 bar, cuttable strands are obtained behind the heated die plate (223° C.; 2 free holes of 2.5 mm each). Hot-cut via rotating knife at a cutting frequency of 123 s$^{-1}$ gives soft granules which are subcooled in a fluidised bed cooler with subsequent crystallisation with air. The following properties are found:

| particle size (minimum-maximum dimension): | 2–5 mm |
|---|---|
| bulk density: | 510–590 kg/l |
| angle of repose (DIN-ISO norm 4324): | 40° |
| flow time (DIN norm 53492): | 2.7 s (φ = 25 mm) |
| evolution of dust (Heubach test): | <0.1 G% after 5 min |
| crystallinity (DSC): | about 95–99% |

EXAMPLE 4

Stabilisation of Polycarbonate (PC)

4985 g of polycarbonate powder (Lexan® 145, producer: General Electric) are mixed with 15 g of the novel stabiliser (product of Example 1, powdered) in a Henschel mixer at room temperature. The powder mixture so obtained is processed to granules using a Göttfert Extrusiometer MP 2.3.0 at a temperature setting of 260/270/280/280° C. at 60 rpm and at a pressure of 61.5 bar and at a shear strength of 47.3 Nm.

2 mm thick plates are produced from the granules so obtained by an injection moulding process (temperature of the die 300° C., temperature of the melt 120° C.).

The plates are exposed to light in an Atlas Weatherometer C165 under the following conditions:

black standard temperature 63° C., relative moisture 60% (dry phase), cycle 102 min. dry/18 min. wet, irradiation 0.35 W/m$^2$ at 340 nm.

The discoloration of the samples is examined before weathering is started, and then at regular intervals, by measuring the yellowness index (YI, method ASTM D 1925). The results are compiled in Table 1; YI(0) indicates the initial colour (=yellowness index before weathering is started).

TABLE 1 yellowness index YI and embrittlement before and during weathering

| stabiliser | weathering time/h | | | |
|---|---|---|---|---|
| | 0 | 500 | 950 | 1214 |
| 0.3% | 6.5 | 6.7 | 11.5 | 16.1 |

The novel stabiliser exhibits excellent effectiveness in the weathering test.

EXAMPLE 5

Preparation of Solid Single-phase Amorphous Mixtures

Mixtures of 2,2'-methylenebis(4-(1,1,3,3-tetramethylbutyl)-6-benzotriazol-2-yl-phenol) (compound 1) and tris(2,4-di-tert-butylphenyl)phosphite (m.p. 180–185° C.) at a weight ratio of 10:1 and 5:1 are melted and chilled by the method described in Example 1.

This gives single-phase amorphous mixtures, $T_G$=65–67° C. (mixture 10:1) and $T_G$=61–63° C. (mixture 5:1) (compare the following Table, samples a and b).

Other single-phase amorphous mixtures are obtained by the above method, 10 g each of a powdered mixture being placed in a boiling glass and homogenised during the melting process under nitrogen at the temperature Ti. The mixtures are then chilled via a surface cooled to Tw under standard atmosphere. The compound used, the test parameters and the resulting glass transition temperature Tg of the amorphous mixture are compiled in the following Table (amounts are given in percent by weight, based on the total weight of the mixture):

| Sample | Compounds and amount | | Ti (° C.) | Tw (° C.) | Tg (° C.) |
|---|---|---|---|---|---|
| a) | 9.1% cmpd. 16, | 90.9% cmpd. 1 | 205 | 18 | 65–67 |
| b) | 16.7% cmpd. 16, | 83.3% cmpd. 1 | 205 | 18 | 61–63 |
| c) | 16.7% cmpd. 16, | 83.3% cmpd. 5 | 245 | 18 | 76–80 |
| d) | 50% cmpd. 16, | 50% cmpd. 6 | 220 | 15 | 62–63 |
| e) | 33.3% cmpd. 16 | 66.7% cmpd. 6 | 225 | 15 | 76–79 |
| f) | 50% cmpd. 13 | 50% cmpd. 2 | 165 | 15 | 48–49 |
| g) | 50% cmpd. 13 | 50% cmpd. 4 | 165 | 15 | 49–51 |
| h) | 50% cmpd. 13 | 50% cmpd. 3 | 180 | 15 | 52–54 |
| i) | 50% cmpd. 13 | 50% cmpd. 5 | 245 | 15 | 62–63 |
| j) | 50% cmpd. 13 | 50% cmpd. 6 | 220 | 15 | 67–68 |
| k) | 50% cmpd. 13 | 50% cmpd. 7 | 230 | 15 | 65–66 |
| l) | 50% cmpd. 13 | 50% cmpd. 10 | 140 | 15 | 45–46 |
| m) | 50% cmpd. 13 | 50% cmpd. 9 | 150 | 15 | 46–47 |
| n) | 50% cmpd. 13 | 50% cmpd. 11 | 150 | 15 | 34–36 |
| o) | 50% cmpd. 13 | 50% cmpd. 1 | 200 | 15 | 56–57 |
| o1) | 50% cmpd. 13 | 50% cmpd. 12 | 135 | 13 | 33–34 |
| o2) | 50% cmpd. 13 | 50% cmpd. 19 | 125 | 13 | 42–44 |
| o3) | 50% cmpd. 13 | 50% cmpd. 15 | 205 | 18 | 60–61 |
| o4) | 50% cmpd. 13 | 50% cmpd. B | 135 | 18 | 40–41 |
| o5) | 10% cmpd. 13 | 90% cmpd. 16 | 195 | 15 | 39–40 |
| o6) | 30% cmpd. 13 | 70% cmpd. 16 | 190 | 15 | 39–40 |
| o7) | 50% cmpd. 13 | 50% cmpd. 16 | 190 | 15 | 41–42 |
| o8) | 70% cmpd. 13 | 30% cmpd. 16 | 170 | 15 | 44–45 |
| o9) | 90% cmpd. 13 | 10% cmpd. 16 | 140 | 15 | 45–46 |
| p) | 33.3% cmpd. A | 66.7% cmpd. 6 | 220 | 15 | 35–36 |
| q) | 15% cmpd. 12; | 28.3% cmpd. 13; 56.7% cmpd. 16 | 200 | 18 | 38–39 |
| r) | 15% cmpd. 12; | 42.5% cmpd. 13; 42.5% cmpd. 16 | 200 | 18 | 40–41 |
| s) | 15% cmpd. 12; | 56.7% cmpd. 16; 28.3% cmpd. 6 | 200 | 18 | 57–59 |
| t) | 15% cmpd. 12; | 42.5% cmpd. 16; 42.5% cmpd. 6 | 225 | 18 | 56–57 | compound A is bis(2,2,6,6-tetramethylpiperidin-4-yl)sebacate
compound B is a phosphonite mixture (CAS-no. 119345-01-6; see introduction examples)

EXAMPLE 5a

Colour-stabilisation of Compound 13

Some of the amorphous mixtures prepared according to Example 5 and comprising compound 13 are subjected to a colour stability test. To this purpose, the samples, which are listed in the following Table, are exposed to daylight in a closed glass vessel under atmospheric conditions. The pure amorphous compound 13 serves as comparison. After the indicated storage time, the discoloration of the samples is visually assessed:

| Sample | 1 Week | 1 Month | 2 Months Storage time |
|---|---|---|---|
| cmpd. 13 | colourless | green | yellowish green |
| f) | colourless | violet | violet |
| g) | colourless | pale green | green |
| h) | colourless | pale green | green |
| i) | colourless | pale green | yellowish green |
| j) | colourless | pale green | green |
| k) | colourless | pale green | yellowish green |
| n) | colourless | pale yellow | yellow |
| o) | colourless | yellow | yellow |
| o1) | colourless | colourless | |
| o2) | colourless | pale yellow | yellow |
| o3) | colourless | colourless | colourless |
| o4) | colourless | colourless | colourless |
| o5) | colourless | white* | white* |
| o6) | colourless | white* | white* |
| o7) | colourless | colourless | colourless |
| o8) | colourless | colourless | colourless |
| o9) | colourless | colourless | |
| q) | colourless | colourless | |
| r) | colourless | colourless | |

*Starting recrystallisation of compound No. 16

When stored, the samples o1, o3–o9, q and r which are colour-stabilised according to this invention show a markedly lower discoloration tendency than the pure compound 13 or than its mixtures with stabilisers other than phosph(on)ites or benzofuranones.

EXAMPLE 6

Use of Subcooled Melts for the Preparation of Granules

A powdered mixture A (resp. B) consisting of compounds 13, 12 and 16 (mixture ratios: see Table 6b) is added gravimetrically at a throughput of 20 kg/h to a laboratory twin-screw extruder (type Bühler DNDF 44). The screw diameter is 44 mm, the length/diameter ratio (l/D) is 24 at 6 barrels, rotational speed of the screws 100 min$^{-1}$. The barrels of the laboratory extruder are tempered such (temperature profile: see Table 6a), that only part of the powder (about 30% by weight) is melted up to barrel 4 at a composition temperature of 130° C. The melt so obtained, consisting of cmpd. 13 (m.p.=115° C.) and 12 (m.p.=132° C.) in a mixture ratio 65:35 (resp. 75:25), is of low viscosity and forms one single microhomogeneous continuous phase, wherein cmpd. 16 (m.p.=186° C.) is dispersed as crystalline phase.

As from barrel 5, the composition is subcooled to about 65° C. (subcooled melt component 25–30% by weight) and is then forced in plastic state (Tg<T<melting point of the continuous phase) through a heated die plate having 6 free holes of 2.5 mm each at a dynamic pressure of 10–12 bar, to give cuttable strands.

Hot-cut via rotating knives at a cutting frequency of 80–100 $s^{-1}$ (cutting length 2–2.5 mm) first gives soft granules (T>Tg), the solidification of which is carried out in a fluidised bed cooler virtually without any subsequent crystallisation.

The granules obtained (see Table 6c) are low-dust and flowable and comprise a single-phase amorphous component (22–27% by weight according to DSC) consisting of cmpd. 13 (55–65% by weight) and cmpd. 12 (35–45% by weight).

Another powdered mixture C (resp. D) consisting of compounds 12, 16 and 6 is processed as described above for the mixtures A and B, but the addition is carried out at a throughput of 22 kg/h and the rotational speed of the screw is 50 $min^{-1}$. Temperature profile and mixture ratios are found in Tables 6a and 6b; the granule properties are compiled in Table 6c. Up to barrel 4, only part of the powder (about 30% by weight) is melted at a composition temperature of about 150° C. A melt of low viscosity consisting of cmpd. 12 (m.p. 132° C.) and 16 (m.p. 186° C.) at a mixture ratio of about 50:50 is obtained as continuous phase, wherein cmpd. 6 (m.p. 220° C.) is dispersed. The composition is subcooled as from barrel 5 to about 120° C. (subcooled melt component 20–25% by weight) and is processed as described above at a dynamic pressure of 7–8 bar (mixture C) or 13–15 bar (mixture D) to strands which are granulated at a cutting frequency of 100 $s^{-1}$. Compound 16 is subsequently crystallised in a fluidised bed cooler. The granules so obtained (see Table 6c) are low-dust, flowable and comprise a single-phase amorphous component (12–15% by weight according to DSC) consisting of cmpd. 12 (about 95% by weight) and cmpd. 16 (about 5% by weight).

TABLE 6a

Temperature profile at the extruder; powder addition in barrel 1

| | Mixture A | Mixture B | Mixture C | Mixture D |
|---|---|---|---|---|
| barrel 1: water | 18° C. | 18° C. | 18° C. | 18° C. |
| barrels 2 + 3: oil | 140° C. | 130° C. | 160° C. | 160° C. |
| barrel 4: oil | 130° C. | 130° C. | 160° C. | 160° C. |
| barrel 5: water | 18° C. | 18° C. | 100° C. (steam) | 70° C. |
| barrel 6: water | 18° C. | 18° C. | 100° C.) (steam) | 105° C. (steam) |
| die plate: oil | 80° C. | 80° C. | 130° C. | 130° C. |

TABLE 6b

Chemical-physical composition of the granules (amounts in % by weight)

| | cmpd. 13 | cmpd. 12 | cmpd. 16 | cmpd. 6 | total | DSC analysis (° C.) |
|---|---|---|---|---|---|---|
| mixture A: | | | | | | |
| amorphous phase | 13–15% | 9–11% | <0.5% | — | 22–26% | Tg = 38–39 |
| crystalline phase | 13–16% | 4–6% | >56% | — | 74–78% | m.p. = 110; 166 |
| total: | 28.3% | 15% | 56.7% | — | 100% | |
| mixture B: | | | | | | |
| amorph. phase | 15–18% | 7–9% | <0.5% | — | 23–27% | Tg = 41–42 |
| cryst. phase | 24.5–27.5% | 6–8% | >42% | — | 73–77% | m.p. = 102; 160 |
| total: | 42.5% | 15% | 42.5% | — | 100% | |
| mixture C: | | | | | | |
| amorphous phase | — | 11–12% | <1% | <0.5% | 11–13% | Tg = 29–30 |
| crystalline phase | — | 3–4% | >56 % | >28 % | 87–89% | m.p. = 122; 160; 180–200 |
| total: | — | 15% | 56.7% | 28.3% | 100% | |
| mixture D: | | | | | | |
| amorphous phase | — | 13.5–14.5% | <1% | <0.5% | 14–15% | Tg = 30–31 |
| crystalline phase | — | 0.5–1.5% | >41.5% | >42% | 75–76% | m.p. = 120; 163; 170–200 |
| total: | — | 15% | 42.5% | 42.5% | 100% | |

TABLE 6c

Properties of the granules

| mixture: | A | B | C and D |
|---|---|---|---|
| particle size (mm; min.-max. dimension): | 1.5–3.5 | 1.5–3.5 | 1.5–3.5 |
| bulk density (kg/l): | 0.52–0.57 | 0.51–0.56 | 0.53–0.56 |
| angle of repose (° ; DIN-ISO-norm 4324): | 37 | 38 | 35 |
| flow time (s; DIN 53492; 15 mm) | 10 | 10.5 | 10 |
| formation of dust (% by weight after 5 min; Heubach test): | 0.22 | 0.26 | 0.24 |
| maximum storage temperature (° C.): | 35 | 35 | 30 |

EXAMPLE 7

Preparation of the β-form of Compound No. 14 by Fluidised Bed Granulation 2 kg of 2-(2-hydroxy-3,5-di-tert-butylphenyl)-5-chlorobenzotriazole (compound No. 14) are placed in a vessel at 190° C. in the form of a melt and are sprayed via a two-fluid nozzle on a fluidised bed consisting of 300 g of the ground compound 14 at an air velocity of 1–1.5 m/s. The product solidifies with formation of granules (agglomeration), consisting to more than 60% of β-form.

EXAMPLE 8

Preparation of the β-form of Compound 14 by Drilling 2-(2-hydroxy-3,5-di-tert-butylphenyl)-5-chlorobenzotriazole (cmpd. 14) is placed in a vessel in the form of a melt and is sprayed at the head of a prill tower and solidified in free fall via air at a temperature of below 156° C. and is then removed at the foot of the tower. The product obtained consists to more than 60% of β-form.

EXAMPLE 9

Preparation of the β-form of Compound 14 by Tempering 100 g of 2-(2-hydroxy-3,5-di-tert-butylphenyl)-5-chlorobenzotriazole (compound No. 14) are kept for 15 h at 145° C. in a laboratory blade drier without adding any solvents. Subsequent X-ray examination shows that the product is obtained to more than 90% in the β-form.

EXAMPLE 10

Preparation of the β-form of Compound 14 by Dissolving and Recrystallisation

In a blade drier, 1600 kg of 2-(2-hydroxy-3,5-di-tert-butylphenyl)-5-chlorobenzotriazole (compound 14) are charged with 240 kg of xylene and the mixture is kept for 5 h at a heating temperature of 145° C. Xylene is then removed by distillation and the contents of the drier are cooled to 100° C., charged with 100 l of water, which is then removed again by distillation, and the product is dried. The product so obtained consists completely of β-form.

On laboratory scale, 750 g of compound 14 are charged in similar manner with 250 g of 2-butanol and 150 g of xylene and the mixture is refluxed for 30 min, the internal temperature being 109° C., and is then brought to 50° C. by hot cooling, filtered and dried. The product so obtained consists completely of β-form.

EXAMPLE 11

Preparation of the Amorphous Form of Compound No. 14

5 g of crystalline powdered 2-(2-hydroxy-3,5-di-tert-butylphenyl)-5-chlorobenzotriazole (compound 14) are placed in a 10 ml test tube and heated under nitrogen in a drying oven. The powder turns into a pale yellow, clear and low viscous melt after 10 to 15 min at 157–159° C. The melt is poured in portions on a stainless steel plate cooled to 0° C. and quickly becomes highly viscous and solidifies spontaneously. Pellets are prepared from part of the melt by dripping on the cooled steel plate. The vitreous composition can be easily separated from the cooling plate and powdered in a cooled mortar. DSC confirms the amorphous structure, $T_g = 22°$ C.

What is claimed is:

1. An amorphous solid or subcooled melt of
   2,2'-methylenebis(4-[1,1,3,3-tetramethylbutyl]-6-benzotriazol-2-yl-phenol);
   bis(2-methyl-4-hydroxy-5-tert-butylphenyl)sulfide;
   N,N'-bis(3-[3',5'-di-tert-butyl-4'-hydroxyphenyl] propionyl)hexamethylenediamine;
   1,3,5-trimethyl-2,4,6-tris(3',5'-di-tert-butyl-4'-hydroxybenzyl)benzene;
   1,3,5-tris(3,5-di-tert-butyl-4-hydroxybenzyl)-1,3,5-triazine-2,4,6(1H, 3H,5H)-trione;
   1,3,5-tris(4-tert-butyl-3-hydroxy-2,6-dimethylbenzyl)1,3,5-triazine-2,4,6-(1H,3H,5H)-trione;
   di(1,2,2,6,6-pentamethylpiperidin-4-yl)-2-(3,5-di-tert-butyl-4-hydroxybenzyl)-2-n-butylmalonate;
   2-(2'-hydroxy-3',5'-bis(1,1-dimethylbenzyl)phenyl) benzotriazole;
   2-(2'-hydroxy-3',5'-di-tert-butylphenyl)benzotriazole;
   2-(2-hydroxy-3,5-di-tert-butylphenyl)-5-chlorobenzotriazole;
   an isomeric mixture of 5,7-di-tert-butyl-3-(3,4-dimethylphenyl)-(9d)-2(3H)-benzofuranone and 5,7-di-tert-butyl-3-(2,3-dimethylphenyl)-(9d)-2(3H)-benzofuranone;
   or of a compound of formula

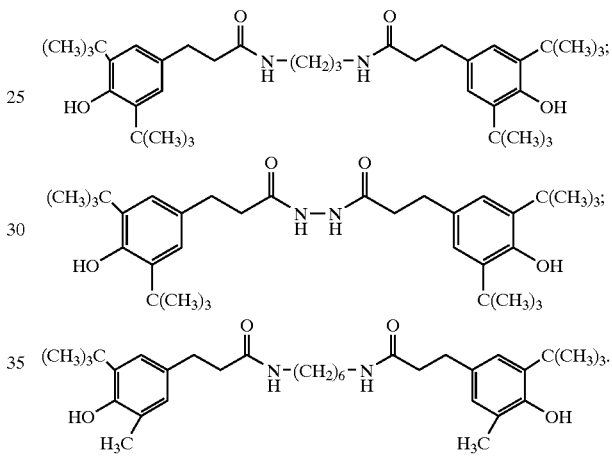

2. A mixture comprising a subcooled melt or amorphous solid of a compound according to claim 1 in an amount from 5 to 100% by weight.

3. A process for the preparation of a subcooled melt according to claim 1, which comprises rapidly cooling the melt to a temperature from the regular melting point to the glass transition temperature of the homogeneous phase.

4. A process for the preparation of an amorphous solid according to claim 1, which comprises chilling the melt or subcooled melt to a temperature below its glass transition temperature.

5. Crystalline β-modification of the compound 14

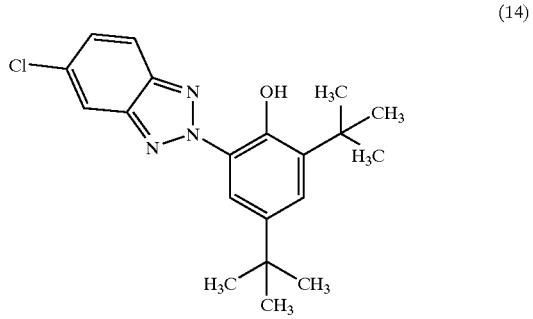

(14)

characterised by the interplanar spacings are $9.4 \cdot 10^{-10}$ m, $4.69 \cdot 10^{-10}$ m, $3.94 \cdot 10^{-10}$ m and $3.79 \cdot 10^{-10}$ m.

6. A mixture consisting of compound 14 of formula

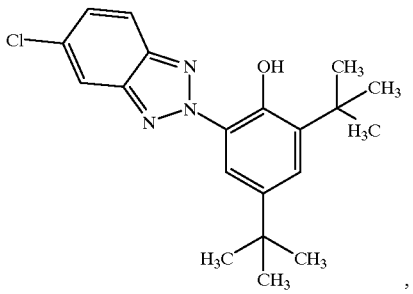

which comprises from 40 up to 100% by weight of β-crystalline form according to claim 5.

7. A process for the preparation of the γ-crystalline form of compound 14 according to claim 6, which comprises crystallising, recrystallising or tempering compound 14 in the temperature range from 95° C. to the melting point and then cooling it rapidly.

8. A process for colour-stabilising amorphous pentaerythritol-tetrakis(3-[3',5'-di-tert-butyl-4'-hydroxyphenyl]propionate), which comprises admixing a stabiliser from the class consisting of the organic phosphites, phosphonites and/or benzofuran-2-ones to a melt consisting of pentaerythritol-tetrakis(3-[3',5'-di-tert-butyl-4'-hydroxyphenyl]propionate) and solidifying the mixture so obtained.

9. Colour-stabilised amorphous pentaerythritol-tetrakis(3-[3',5'-di-tert-butyl-4'-hydroxy-phenyl]propionate) containing a sufficient stabilising amount of a stabiliser from the class consisting of the organic phosphites, phosphonites and/or benzofuran-2-ones.

10. A stabiliser composition, which comprises
a) pentaerythritol-tetrakis(3-[3',5'-di-tert-butyl-4'-hydroxyphenyl]propionate), and
b) a compound of the benzofuran-2-one type.

11. A composition, which comprises
A) an organic material susceptible to oxidative, thermal or/and actinic degradation or build-up, and
B) the amorphous form of a compound according to claim 1, the β-crystalline form of compound 14

(14)

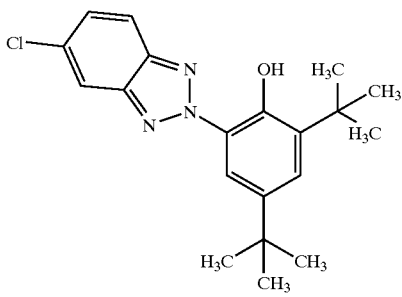

characterised by interplanar spacings at 9.4·10⁻¹⁰ m, 4.69·10⁻¹⁰ m, 3.94·10⁻¹⁰ m and 3.79·10⁻¹⁰ m and/or the stabiliser composition which comprises a) pentaerythritol-tetrakis(3-[3',5'-di-tert-butyl-4'-hydroxyphenyl]propionate), and b) a compound of the benzofuran-2-one type as stabiliser.

12. A process for stabilising organic material against oxidative, thermal or actinic degradation or build-up, which comprises adding to the material the amorphous form of a compound according to claim 1, the β-crystalline form of compound 14

(14)

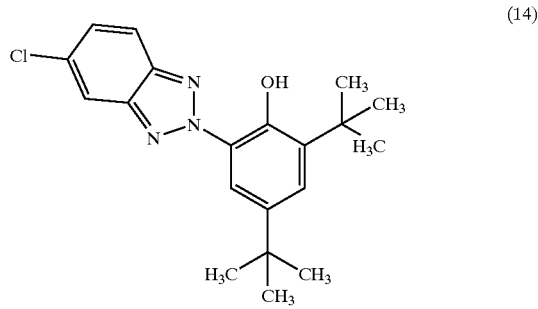

characterised by interplanar spacings at 9.4·10⁻¹⁰ m, 4.69·10⁻¹⁰ m, 3.94·10⁻¹⁰ m and 3.79·10⁻¹⁰ m and/or the stabiliser composition which comprises a) pentaerythritol-tetrakis(3-[3',5'-di-tert-butyl-4'-hydroxyphenyl]propionate), and b) a compound of the benzofuran-2-one type as stabiliser.

13. A process according to claim 12, wherein 0.01 to 15 parts by weight of the stabiliser are added to 100 parts by weight of organic material to be stabilised.

14. A process according to claim 12, wherein the organic material is a synthetic thermoplastic polymer.

15. A process according to claim 12, wherein a customary additive is added as further component.

16. Granules obtained by a process which comprises extruding a subcooled melt consisting essentially of an organic compound having a molecular weight of 200 to 1500 g/mol, or the plastic composition consisting of the mixture of the subcooled melt and a further component, which is selected from compounds of the subcooled melt in crystalline form and other conventional additives.

17. A process for the preparation of a mixture comprising a subcooled melt according to claim 2, which comprises rapidly cooling the melt to a temperature from the regular melting point to the glass transition temperature of the homogeneous phase.

18. A process for the preparation of a mixture comprising an amorphous solid according to claim 2, which comprises chilling the melt or subcooled melt to a temperature below its glass transition temperature.

* * * * *